United States Patent [19]

Clayton et al.

[11] 4,088,127
[45] May 9, 1978

[54] MASSAGE APPLIANCE

[76] Inventors: Donna M. Clayton, 1691 Hyacinth La.; Donna J. Martinez, 1803 Rosswood Dr., both of San Jose, Calif. 95124

[21] Appl. No.: 761,013

[22] Filed: Jan. 21, 1977

[51] Int. Cl.² ............................................. A61H 29/00
[52] U.S. Cl. ................................................... 128/24.1
[58] Field of Search .................. 128/24.1, 67, 62, 254, 128/258, 403, 64, 65; 4/184; 15/227, 110

[56] References Cited

U.S. PATENT DOCUMENTS

| 1,161,719 | 11/1915 | Norton | 15/227 |
| 1,431,336 | 10/1922 | Smith | 15/227 |
| 2,233,686 | 3/1941 | Topjian | 15/227 |
| 2,502,182 | 3/1950 | Strauch | 128/24.1 |
| 2,694,396 | 11/1954 | Paschal | 128/67 |

*Primary Examiner*—Lawrence W. Trapp
*Attorney, Agent, or Firm*—Gerald L. Moore

[57] ABSTRACT

A massage appliance which can be fitted on the hand so that a pliable fluid-filled bag is held in place for contacting the body.

5 Claims, 3 Drawing Figures

U.S.Patent    May 9, 1978    4,088,127

MASSAGE APPLIANCE

BACKGROUND OF THE INVENTION

For massaging the body, pressure must be applied in a gentle manner following the various contours and configurations of the body portions being massaged. In addition, it is sometimes advantageous to apply heat or cold to the body portions. The subject invention combines the functions of providing a supple and pliable surface for contact with the body while also enabling one to selectively apply heat or cold to the body areas being massaged.

SUMMARY OF THE INVENTION

A massage appliance comprising a mitt which can be fit over the hand to at least partially cover the palm. Fixed to the palm side of the mitt is a pliable sealed bag filled with fluid. By placing the mitt on one hand the bag can be rubbed over various parts of the body to be massaged and if the application of heat or cold is desired, the fluid within the bag can be heated or cooled for that purpose.

DESCRIPTION OF THE INVENTION

For various aches and pain and for comfort, it is frequently advantageous to massage various parts of the body. A massage involves the rubbing or manipulating of the body surface or muscles with gentle pressure usually applied by the hands. It is important that the pressure be gentle and uniform and be applied in a manner to conform with the contours of the body. In addition it is frequently advantageous to apply heat or cold compresses to the body to stimulate blood circulation or to sooth various aches and pains. The appliance which is the subject of this invention is particularly adapted for the purposes described.

Figure 1:
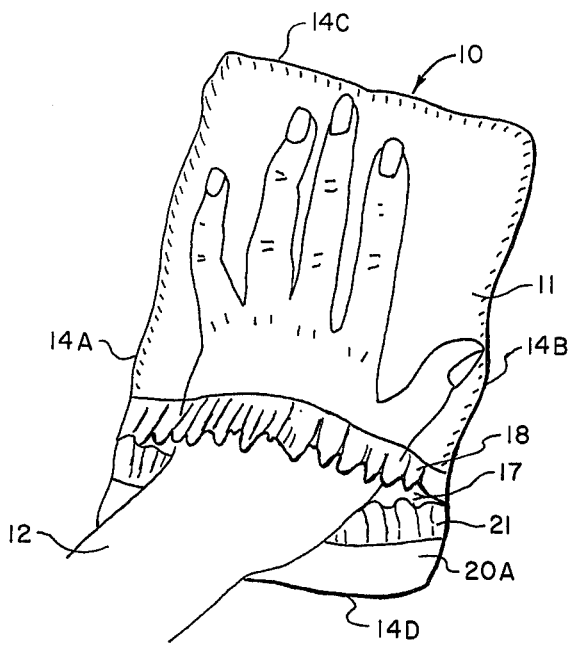
FIG. 1 is a perspective view of the massage appliance placed on a hand.
Figure 2:
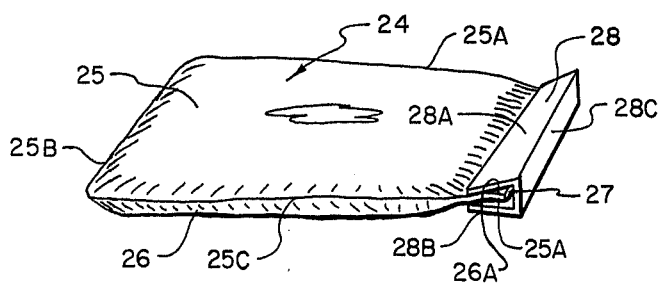
FIG. 2 is a perspective view of the fluid-filled sack.
Figure 3:
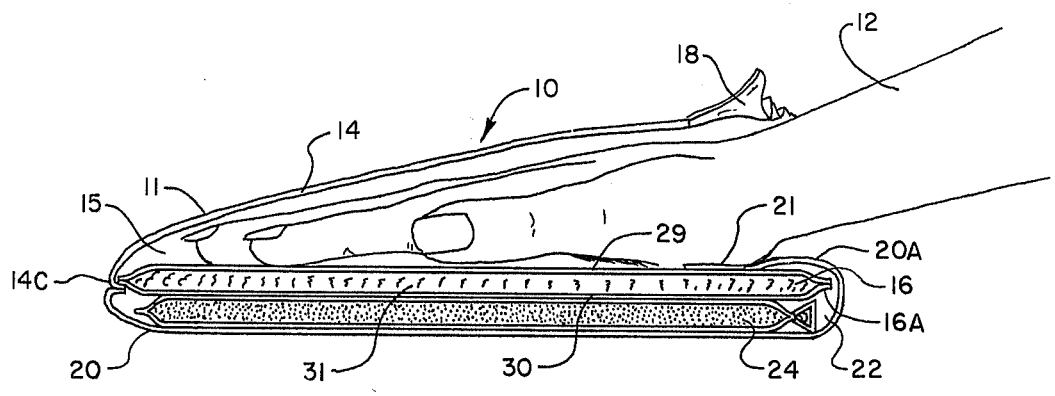
FIG. 3 is a cross-sectional view of the appliance with a hand inserted.

As shown in FIGS. 1 and 3, the appliance 10 of the subject invention comprises a mitt 11 formed to fit on a hand 12 of the person doing the massaging. In the present instance, the mitt 11 comprises a first panel 14 forming an outer cover. The cover can be pulled up over the back of a hand as it is pushed into an inner pocket 15 of sufficient size to receive the total hand with the fingers generally extending together. Thus in the particular embodiment described, the mitt is approximately five inches wide and seven inches long and is rectangular in configuration. Preferebly this first panel is made of a suitable cloth material.

The pocket 15 in this embodiment is formed by joining the outer cover 14 at the edges 14A and 14B and at the end 14C to a pad 16 having the approximate size of the mitt. Thus the pad in this embodiment completely covers the palm of the hand. Also as shown, the end 18 of the cover 14 forms an opening 17 preferably extending parallel to the edge 14D and spaced slightly therefrom, into which the hand can be inserted. If desired, the cover end 18 can include elastic (not shown) so as to conform about the wrist of the user and tend to hold the mitt on the hand.

In the embodiment shown, there is fixed to the edge 14C of the cover 14 a second cloth panel 20 which extends parallel to the pad 16 on the side opposite from the cover 14. This second panel preferably is fixed to the pad and the panel 14 at the edges 14A and 14B. The end 20A extends around the end 16A of the pad and is terminated at an elastic band 21 which holds it closely adjacent to the pad 16. Thus there is formed between the pad 16 and the panel 20 a second pocket 22 which is accessible by pulling the second panel end 21 down around the pad end 16A for exposure of the opening thereto.

Placed in this second pocket 22 is a bag 24 shown in FIG. 3. This bag preferably is made of a pliable and flexible material such as plastic to form a watertight container. It can be formed by joining a top sheet 25 and a bottom sheet 26 at the edges 25A, 25B and 25C to form water-tight seals leaving an opening 27 formed between the extending and unjoined sheet ends 25A and 26A. When the bag is filled with a fluic it serves as a contact member for the body portion being massaged. The bag 24 is filled with a liquid such as water and thereafter sealed by the placement of a plastic clip 28 across the edges 25A and 26A of the side panels. This plastic clip has extending ends 28A and 28B which are spring biased together by the end 28C so as to hold the edges of the bag and seal against the escape of any liquid in the bag. If desired the extending edges 25A and 26A can be folded over prior to placement of the clip 28 to further assure against leakage from the bag.

The bag 24 filled with liquid is preferably in a flat planar configuration having a rectangular form slightly less in dimensions than the pocket 22. Thus the bag can be inserted into the pocket 22 and the second panel end 21 be pulled around the pad 16 to maintain the bag in the mitt. With the bag so inserted and the mitt placed on the hand as shown in FIGS. 1 and 3, the bag forms a pliable member held against the palm of the hand in position to be rubbed on the body for effecting a massage. The bag conforms both to the contours of the palm because of being filled with a liquid and also will easily bend about the contours of the body portion being massaged to give a soothing and even pressure necessary for an effective massage treatment.

In accordance with another feature of the invention the bag 24 can be filled with either a heated or a cooled fluid such that when the appliance is used in a massage either a heating or cooling effect is realized on the portion of the body being rubbed. In the usual instance a heated fluid will be placed in the bag for massaging sore muscles, et cetera. The pad 16 preferably is made of a pair of panels 29 and 30 (FIG. 3) which are joined together at the edges forming a void 31 therebetween filled with a soft padding such as cotton. Thus the pliability of the mitt is not affected yet an insulating barrier is provided between the hand and the bag. This insulating barrier is necessary because the hand is held in constant contact with the bag which can result in some discomfort if the temperature of the fluid is sufficiently hot or cold. The person being massaged is not necessarily affected in the same manner because the bag is in constant movement relative to the body portion being massaged and therefore is not held in constant contact with any one part long enough for there to be a sufficient heat transfer to render discomfort. Thus the insulation between the hand and the bag is a necessary convenience for the massage appliance.

The invention claimed:

1. A massage appliance comprising:
   a mitt forming a pocket into which a hand can be inserted and having a pad adjacent the palm of the hand;
   a pliable sealed bag filled with fluid and being of an approximate size to cover at least a portion of the hand; and
   means fixing said bag to the palm side of the mitt whereby said mitt can be used to massage the parts of the body by bringing the sealed bag into contact therewith.

2. A massage appliance as defined in claim 1 including means for removing fluid from and inserting fluid back into the bag.

3. A massage appliance as defined in claim 2 wherein the pad between the fluid bag and the pocket for the hand is made of insulating material to serve as a temperature barrier between the hand and the bag.

4. A massage appliance comprising, in combination:
   a first panel;
   a second panel;
   means fixing the first and second panel together at three edges to form a pocket therebetween;
   a pad fixed within said pocket to divide the pocket into first and second pockets; and
   a pliable fluid tight container filled with fluid and fitted into said second pocket whereby the hand can be inserted in the first pocket and the pliable fluid container serve as a contact member for effecting a massage on the body.

5. A massage appliance as defined in claim 4 wherein said pad is made of insulating material to provide a temperature insulating barrier between the first and second pockets.

* * * * *